United States Patent [19]

O'Connor et al.

[11] 4,123,522

[45] Oct. 31, 1978

[54] CONTROL OF BLOAT IN RUMINANTS

[75] Inventors: Jeremiah J. O'Connor, Flemington; Raymond R. Pilote, Somerset, both of N.J.; Wayne H. Linkenheimer, Washington Crossing, Pa.

[73] Assignee: E. R. Squibb & Sons, Inc., Princeton, N.J.

[21] Appl. No.: 806,793

[22] Filed: Jun. 15, 1977

[51] Int. Cl.$^2$ .............................................. A61K 35/70
[52] U.S. Cl. ..................................................... 424/116
[58] Field of Search ......................................... 424/116

[56] References Cited

U.S. PATENT DOCUMENTS

| | | | |
|---|---|---|---|
| 3,234,086 | 2/1966 | Hartman et al. | 424/271 |
| 3,248,289 | 4/1966 | Shinozaki et al. | 424/329 |
| 3,465,083 | 9/1969 | Bartley et al. | 424/342 |
| 3,686,416 | 8/1972 | Myer et al. | 424/329 |
| 3,814,795 | 6/1974 | Arima et al. | 424/116 |
| 3,868,448 | 2/1975 | Hahn et al. | 424/94 |
| 3,876,778 | 4/1975 | Szanto et al. | 424/181 |
| 3,917,514 | 11/1975 | Mimura et al. | 195/80 R |

OTHER PUBLICATIONS

Bartley et al.—J. Animal Sci., vol. 41, (1975), pp. 752-759.
Johnson et al.—J. Animal Sci., vol. 19, (1960), pp. 735-744.
Grosskopf—Afr. Vet. Med. Assn., vol. 35, (1964), pp. 169-178.
Clarke—Nature, vol. 205, (1965), pp. 95-96.
Kodras—Am. J. Vet. Res., vol. 27, (1966), pp. 629-632.
Willard et al.—Applied Microbiology, vol. 15, (1967), pp. 1014-1019.
Davis et al.,—Can. J. Animal Sci., vol. 52, (1972), pp. 329-335.
Clarke et al.—J. Dairy Sci., vol. 57, (1972), pp. 753-785.
Howarth—Can. Vet. J., vol. 16, (1975), pp. 281-294.
Meyer et al.—J. of Animal Science, vol. 34, Jan.-Mar. 1972, p. 234.

*Primary Examiner*—Sam Rosen
*Attorney, Agent, or Firm*—Lawrence S. Levinson; Merle J. Smith; Stephen B. Davis

[57] ABSTRACT

Bloat, particularly feedlot bloat, in ruminants is treated and controlled by the administration of the antibiotic S 15-1. This antibiotic can also be employed to lessen digestive disturbances caused when the diet of the ruminant is changed.

12 Claims, No Drawings

CONTROL OF BLOAT IN RUMINANTS

BACKGROUND OF THE INVENTION

Bloat is a digestive disorder of ruminants that develops as rumen microbes degrade readily available nutrients. The rapidly formed fermentation gases are trapped in the rumen digesta and produce a stable foam. The accumulation of this foam prevents eructation and the pressure from the trapped gas distends the rumen. Bloat is characterized as pasture or feedlot bloat depending upon the diet of the ruminant. Feedlot bloat develops when ruminants are fed large amount of grain which supply easily digestible carbohydrates from which excessive amounts of fermentation gases are produced. Pasture bloat is most commonly associated with the rapid consumption of large amounts of fresh green legumes.

Previous attempts to treat and cure bloat have included the administration of surface active compounds. For example, Shinozaki et al in U.S. Pat. No. 3,248,289 discloses the use of certain polyoxypropylene-polyoxyethylene polymeric non-ionic surfactants, Bartley et al in U.S. Pat. No. 3,465,083 discloses the use of a specific polyoxypropylene-polyoxyethylene surfactant known as poloxalene, and Myer et al in U.S. Pat. No. 3,686,416 discloses the use of a dimethyl dialkyl quaternary ammonium compound to control feedlot bloat.

It has also been proposed to treat bloat by the administration of antibiotics such as penicillin or combinations of penicillin and macrolide antibiotics such as erthromycin and tylosin as note Johnson et al, J. Animal Sci., Vol. 19, p. 739–744 (1960) and Hartman et al in U.S. Pat. No. 3,234,086.

Hahn et al in U.S. Pat. No. 3,868,448 disclose the prevention and treatment of bloat by administering an enzyme obtained from the fermentation of a specific *Streptomyces griseus* to the ruminant.

It has been suggested that protozoa present in the rumen may be a cause of bloat as note Clarke, Nature, Vol. 205, p. 95–96 (1965) and Kodras, Am. J. Vet. Res., Vol. 27, p. 629–632 (1966). Accordingly, numerous agents including antimalarials, anthelmintics, arsenicals, inorganic compounds, antibiotics and biocides, surface active agents, neuromuscular agents, hormonal agents, and cyclic nitrogen compounds were screened in vitro for antiprotozoal activity in ruminal fluid by Willard et al, Appl. Microbiol., Vol. 15, p. 1014–1019 (1967).

SUMMARY OF THE INVENTION

This invention is directed to the discovery that the antibiotic S 15-1 is useful for treating and controlling bloat in ruminants because of its antiprotozoal activity. Also, this compound can be employed in a prophylactic manner to lessen digestive disturbances caused by sudden changes in the diet of the ruminant.

DETAILED DESCRIPTION OF THE INVENTION

The antibiotic S 15-1 is a number of the streptothricin family and its preparation and characteristics are disclosed by Arima et al in U.S. Pat. No. 3,814,795 and by Mimura et al in U.S. Pat. No. 3,917,514. S 15-1 is described as possessing antimicrobial activity against gram-positive and gram-negative organisms and of inhibiting the growth in tissue culture of virus such as Newcastle disease virus. Additionally, Szanto et al in U.S. Pat. No. 3,876,778 disclose the use of S 15-1 as a taeniacidal agent.

The antibiotic S 15-1 due to its antiprotozoa activity can be employed to control and reduce the severity of bloat, particularly feedlot bloat, in ruminants, particularly cattle. For this purpose, the antibiotic S 15-1 should be administered to the bloated ruminant in a dosage range of from about 0.5 mg. per kg. to about 8 mg. per kg. of body weight per day in one or more doses for from about 3 to about 21 days. Of course, the particular dose and length of time of treatment will depend upon the severity of the bloat.

The antibiotic S 15-1 can also be employed in a prophylactic manner so as to lessen the likelihood of the ruminant developing bloat, particularly feedlot bloat. Also, the antibiotic S 15-1 can be administered to ruminants, particularly cattle, that are being fed a high concentration diet so as to shorten the adaptation period and lessen the chance of their developing digestive disturbances. For such purposes the antibiotic S 15-1 should be administered to the ruminant in an amount of from about 0.05 mg. per kg. to about 4 mg. per kg. of body weight per day in one or more doses.

The antibiotic S 15-1 is formulated and administered according to conventional pharmaceutical and veterinary practice. Thus, the antibiotic can be combined with a drug compatible carrier such as lactose and formed into a bolus pettet or filled into a gelatin capsule which can then be forced down the ruminant's throat by a conventional bolus gun. The antibiotic can also be mixed with a pharmaceutically acceptable carrier such as lactose to form a feed supplement that can be incorporated in the ruminant feed in the desired concentration, it can be added to the ruminant's drinking water, it can be incorporated into salt licks or various mineral mixtures. When the ruminant being treated is already suffering with bloat, it is preferred to administer the antibiotic as a bolus or capsule since the ruminant may refuse to eat. Other veterinary medications such as general purpose antibiotics can be included with the above formulations.

The following examples demonstrate the use of the antibiotic S 15-1 in treating ruminants suffering with feedlot bloat.

EXAMPLE 1

This example demonstrates the effectiveness of S 15-1 against rumen protozoa. Three fistulated sheep are each given 100 mg. of the antibiotic S 15-1 per day for 7 days. After 7 days, samples of the rumen fluid are taken and the number of protozoa are counted using a McMaster counting chamber. The results are shown in Table 1.

Table 1

|  | Dose mg./head/day | Number of Protozoa (Average for 3 Sheep) $\times 10^5$/ml |
|---|---|---|
| Control | — | 2.86 |
| S 15-1 | 100 | 0.14 |

EXAMPLE 2

Two rumen fistulated adult cattle are fed a feedlot bloat provoking ration until frothy bloat develops. Once good bloat is established, rumen samples are obtained from a sampling tube placed in a fixed location in the ventral rumen. Three rumen samples are taken on alternate days before administration of the antibiotic S 15-1. The antibiotic is given to both animals at a rate of 750 mg. per cow per day for 15 days. The antibiotic is administered for 15 days and the cows are sampled on days 4, 10, and 15. The following information is obtained from each sample and listed in Table 2.

2 = froth under pressure but no abdominal distention of the left flank
3 = froth and definite distention of the left flank
4 = distention of both left and right flanks
5 = distress symptoms evident.

Table 2

| Sample | Bloat Score | Slime mg/100 ml. | Rumen pH | Number Bacteria $\times 10^9$/ml. | Number Protozoa $\times 10^3$/ml. | Holotrichs (%) | Oligotrichs (%) |
|---|---|---|---|---|---|---|---|
| COW 1 | | | | | | | |
| Pretreatment | | | | | | | |
| 1 | 2 | 47.0 | 6.88 | 5.2 | 41.3 | 8.1 | 91.9 |
| 2 | 3 | 33.5 | 6.68 | 5.45 | 43.4 | 10.2 | 89.8 |
| 3 | 3 | 28.5 | 6.63 | 7.45 | 31.3 | 12.6 | 87.4 |
| Treatment | | | | | | | |
| day 4 | 3 | 73.3 | 6.41 | 7.10 | 3.35 | 98.1 | 1.9 |
| day 10 | 0 | 43.0 | 7.02 | 5.33 | 0.19 | 100 | 0 |
| day 15 | 0 | 0 | 7.12 | 2.44 | 0.06 | 100 | 0 |
| COW 2 | | | | | | | |
| Pretreatment | | | | | | | |
| 1 | 3 | 65.0 | 5.95 | 14.45 | 103 | 3.2 | 96.8 |
| 2 | 3 | 125.8 | 5.97 | 7.80 | 103 | 1.8 | 98.2 |
| 3 | 3 | 74.3 | 6.15 | 11.65 | 63.9 | 5.0 | 95.0 |
| Treatment | | | | | | | |
| day 4 | 2 | 137.0 | 5.44 | 21.40 | 2.85 | 61.1 | 38.9 |
| day 10 | 2 | 80.3 | 5.81 | 9.33 | 0.44 | 100 | 0 |
| day 15 | 2 | 36.5 | 5.83 | 16.40 | 0.32 | 100 | 0 |

A. Protozoal Count 250 ml. of rumen fluid is removed with a dosing syringe inserted in the sampling tube passed through the cap of the rumen cannula plug. This fluid is strained through four layers of cheesecloth, mixed, and 1 ml. samples are diluted with a 50% acetate and glycerol buffer solution. The protozoa are counted using a counting chamber designed specifically for protozoa. The two orders of protozoa (Holotriches and Oligotrichs) are counted and the percentages of each are listed.

B. Bacterial Counts

The total number of rumen bacteria are counted using a Petroff-Hauser chamber.

C. Rumen pH

The pH is measured immediately after sampling.

D. Rumen Slime

The rumen slime is measured using the ethanol precipitation procedure of Gutierrez, Appl. Microbiol., Vol. 9, p. 209 (1961).

E. Bloat Score

Bloat score is determined using a scale of 0 (no bloat) to 5 (severe bloat). The detailed scale is as follows:

0 = no froth
1 = froth but no abdominal distention of the left flank

What is claimed is:
1. The method of treating bloat in ruminants comprising administering an effective amount of the antibiotic S 15-1 to the bloated ruminant.
2. The method of claim 1 wherein the antibiotic is administered in an amount of from about 0.5 mg./kg. to about 8 mg./kg. of body weight per day for from about 3 to about 21 days.
3. The method of claim 2 wherein the bloat is feedlot bloat.
4. The method of claim 3 wherein the antibiotic S 15-1 is administered orally.
5. The method of claim 4 wherein the ruminants are cattle.
6. The method of claim 4 wherein the ruminants are sheep.
7. The method of preventing bloat and digestive disturbances in ruminants comprising administering an effective amount of the antibiotic S 15-1 to the healthy ruminant.
8. The method of claim 7 wherein the antibiotic is administered in an amount of from about 0.05 mg./kg. to about 4 mg./kg. of body weight per day.
9. The method of claim 8 wherein the bloat is feedlot bloat.
10. The method of claim 9 wherein the antibiotic S 15-1 is administered orally.
11. The method of claim 10 wherein the ruminants are cattle.
12. The method of claim 10 wherein the ruminants are sheep.

* * * * *